US00PP34255P2

(12) United States Plant Patent
Hansen

(10) Patent No.: US PP34,255 P2
(45) Date of Patent: May 17, 2022

(54) ***X MANGAVE* PLANT NAMED 'SWEET TOOTH'**

(50) Latin Name: **x *Mangave* hybrid**
Varietal Denomination: Sweet Tooth

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,984

(22) Filed: Jan. 10, 2022

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 6/12; A01H 5/12
See application file for complete search history.

*Primary Examiner* — Keith O. Robinson

(57) ABSTRACT

A new and unique x *Mangave* plant named 'Sweet Tooth' characterized by a compact, rounded mound of thick, fleshy, lanceolate, glaucous, sarcous leaves that are mostly flat, slightly-arching and terminate in a large, firm, apical spine. The leaves have numerous large, slightly flexible, marginal teeth curving toward base. Foliage is variegated with dark green margins and the leaf centers becoming striated with grey and celadon. The new plant is suitable for the garden or as a potted plant in the garden or home.

2 Drawing Sheets

Botanical classification: x *Mangave* hybrid.
Variety denomination: 'Sweet Tooth'.

BACKGROUND OF THE INVENTION

The present invention relates to the new and distinct x *Mangave* hybrid plant, x *Mangave* 'Sweet Tooth' that was discovered by the inventor at a wholesale perennial nursery in Zeeland, Mich., USA as whole plant mutation of x *Mangave* 'Tooth Fairy' U.S. Plant Pat. No. 29,599. The new mutation was discovered on Jul. 2, 2018. Through trials at the same nursery the plant was assigned the code number 18-SP-MANG-699-A. The new plant has been successfully asexually propagated by division plantlets following coring at the same nursery in Zeeland, Mich. originally in 2021. The asexual propagation has been found to produce stable and identical plants that maintain all the unique characteristics of the original plant.

BRIEF SUMMARY OF THE INVENTION x *Mangave* 'Sweet Tooth' differs from its parent as well as all other *Manfreda, Agave* and x *Mangave* known to the applicant. The sport parent, 'Tooth Fairy', does not have the variegated foliage with the center streaked with light minty-green streaks and oblong purplish-red spotting.

The nearest comparison plants are: *Agave deserti* 'Snow Devil' (not patented); and x *Mangave* 'Carnival' U.S. Plant Pat. No. 31,249, 'Dragon Lady' U.S. Plant Pat. No. 33,985, 'Frosted Elegance' U.S. Plant Pat. No. 32,289, 'Pineapple Upsidedown Cake' (not patented), 'Bloodlines' (not patented), 'Queen for a Day' U.S. Plant Pat. No. 32,711, 'Arctic Fox' (not patented) and 'Frosted Jade' U.S. Plant patent application Ser. No. 17/300,994.

'Snow Devil' has a similar variegation and size, wider, flatter and thicker leaves with larger teeth that are more green and pointing more outwardly rather than backward.

'Carnival' has a broader habit, longer, flatter leaves with a solid yellow center, dark green margins and smaller more flexible marginal teeth. 'Dragon Lady' has a broader habit and the leaves are longer, more folded and more sinuate with small marginal teeth, dark green margins yellowish center with both margins and centers heavily spotted with reddish-purple. 'Frosted Elegance' is a much larger and flatter plant with longer leaves that have a more grayed-green margin and center is not striated or streaked and does not show purplish-red spotting. 'Pineapple Upsidedown Cake' has a larger and broader habit, narrower leaves that are solid yellowish with reddish spotting in the center with a deep green margin and small flexible marginal teeth. 'Bloodlines' has narrower leaves with an intense purple margin without the striation or streaking in the center. 'Queen for a Day' has broader leaves that are grey-green with reddish spotting with a purplish margin and smaller, flexible, marginal teeth. 'Arctic Fox' has a larger habit, thinner and more narrow foliage with smaller, pale-green, marginal teeth, and the center variegation is a solid whitish-green, the margin is medium green and the leaves have greyed-purple spotting with high ultraviolet light exposure. 'Frosted Jade' has a solid mint-green variegated leaf center with smaller more flexible teeth.

'Sweet Tooth' is unique from all the above cultivars and all *Agave*, x *Mangave* and *Manfreda* known to the inventor by the following combined traits:

1. Compact, rounded mound of thick, lanceolate, glaucous, slightly arching, sarcous leaves;
2. Leaf margins develop large, colorful, apical spines and marginal teeth that are slightly flexible and change colors and the leaves mature;
3. Marginal teeth leave an impression on upper and lower leaves above and below from when tightly compressed in shoot tip;

4. Leaf centers are variegated with grey and celadon striations;
5. Moderate to slower growth rate;

BRIEF DESCRIPTION OF THE DRAWING

The photograph of x *Mangave* 'Sweet Tooth' demonstrates the overall appearance of the new plant including the unique traits as a three-year-old plant grown in a greenhouse in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
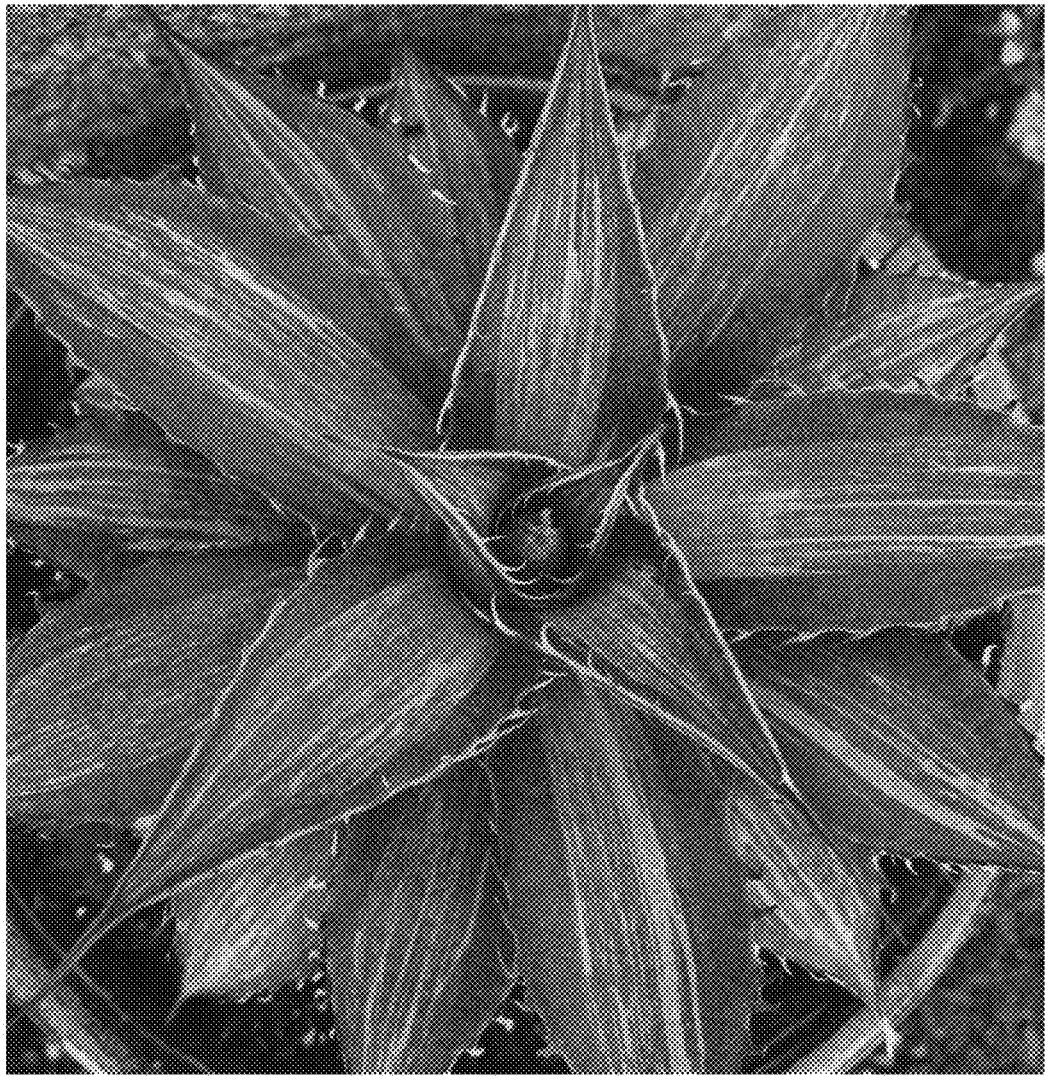
FIG. 1 shows a side view of the new plant.
Figure 2:
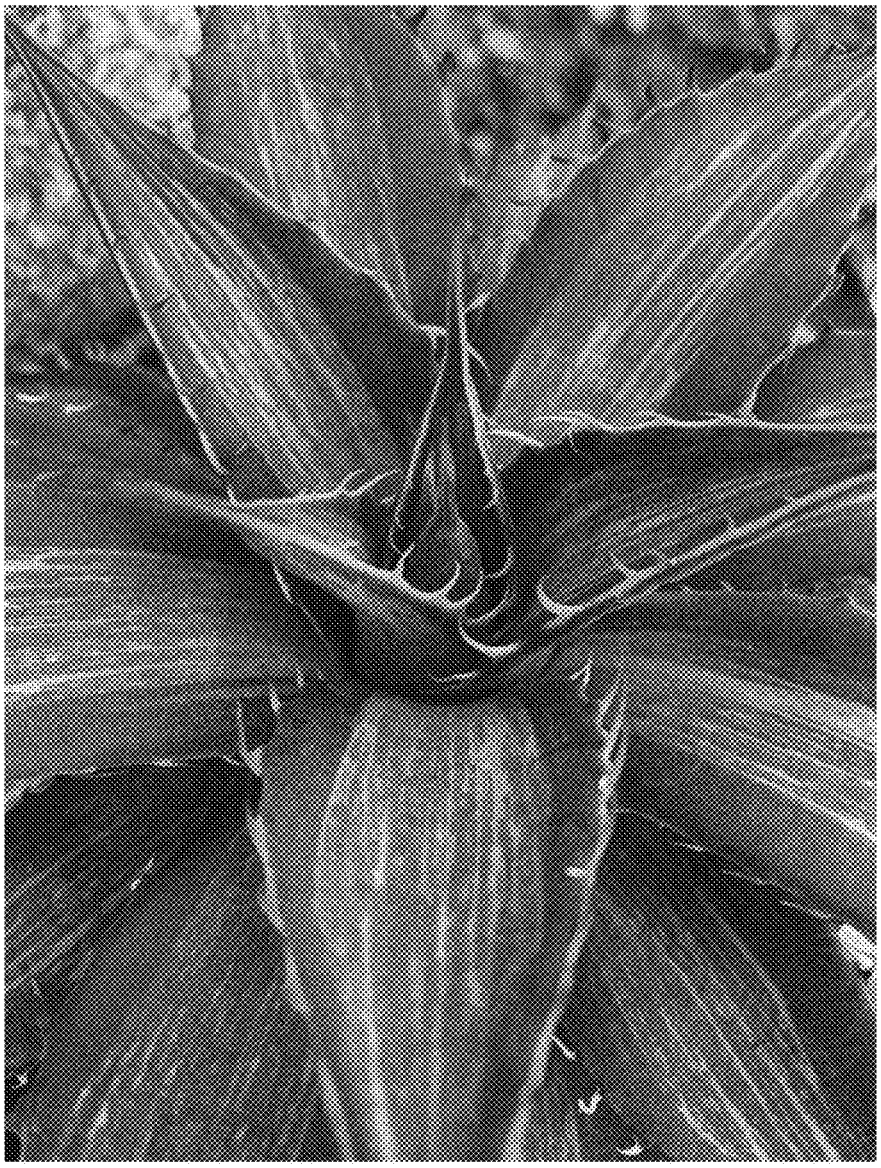
FIG. 2 shows a close-up of the variegation coloration and marginal teeth.

The following descriptions and color references are based on the 2015 edition of The Royal Horticultural Society Colour Chart except where common dictionary terms are used. The new plant, x *Mangave* 'Sweet Tooth', has not been observed under all possible environments. The phenotype may vary slightly with different environmental conditions, such as temperature, light, fertility, moisture and maturity levels, but without any change in the genotype. The following observations and size descriptions are of a three-year-old plant in a greenhouse in Zeeland, Mich. with supplemental water and fertilizer as needed.

Parentage: Whole plant mutation of 'Tooth Fairy';

Propagation: By plantlet division following coring;

Time to initiate roots: About 28 days;

Growth rate: Moderate to slow;

Crop time: About 24 to 28 weeks to finish in a 3.8-liter container from a 35 mm tissue culture growing at about 21° C.;

Rooting habit: Fleshy, lightly branching, with roots up to 15 cm long;

Root color: Between RHS 161C and RHS NN155C;

Plant shape and habit: Succulent, frost-tender herbaceous perennial with basal rosettes of about 34 leaves radially emerging outwardly from central stem, producing a radially-symmetrical, rounded mound with age;

Plant size: Foliage height about 11 cm tall from soil line to the top of the leaves and about 20 cm wide at the widest point just above soil level;

Stem: To about 2.5 cm across and about 2.0 cm long; covered with foliage, not visible;

Foliage description: Lanceolate; simple; sessile; bi-laterally symmetrical; sarcous; apex narrowly acute with firm, sharp, terminal spine; base truncate; lightly glaucous adaxial and abaxial; margins flat, with semi-flexible, flexuose to curved pointed teeth;

Foliage size: To about 8 cm long, 3 cm wide near middle and about 12 mm thick near base;

Apical spine: About 14 mm long and 2 mm wide at base;

Marginal teeth: Small, flexible even when mature; to about 5 mm long from margin and 2.5 mm wide at base, spacing to about 5 mm apart near center and;

Variegation width: Centers to about 23 mm wide on adaxial side and 25 mm wide on abaxial side;

Foliage fragrance: None observed;

Leaf number: About 34 per plant;

Leaf blade color:

*Adaxial*.—Young and mature leaf margins between RHS 139A and RHS N137A.

*Abaxial*.—Young leaf margins between RHS 139A and RHS N137A.

*Adaxial*.—Young leaf centers with striations of variable lengths and sizes of between RHS 147D and RHS 138B and between RHS 190D and RHS 192D.

*Abaxial*.—Young leaf centers with striations of variable lengths and sizes of between RHS 147D and RHS 138B and between RHS 190D and RHS 192D.

*Adaxial*.—Mature leaf margins between RHS 189C and RHS 139A.

*Abaxial*.—Mature leaf margins nearest RHS N138A.

*Adaxial*.—Mature leaf centers with striations of variable lengths and sizes of nearest RHS 138B and between RHS 190D and RHS 188D.

*Abaxial*.—Mature leaf centers with striations of variable lengths and sizes of nearest RHS 138B and between RHS 190D and RHS 192D.

*Teeth*.—Variable with age, beginning between RHS 162D and RHS 158A, transitioning through RHS 163B, RHS 171B and RHS N172A, maturing between RHS 178A and RHS 183A.

*Apical spine*.—Nearest RHS 178A as maturing and between RHS 183A and RHS 200B when mature.

Petiole: Leaves sessile;

Veins: Parallel; not distinct abaxial or adaxial;

Flower description: Not yet observed;

Fruit and seed: Not yet observed;

Disease resistance: X *Mangave* 'Sweet Tooth' has not been observed to be resistant or susceptible to diseases beyond that which is normal for x *Mangave, Agave* or *Manfreda*.

Growing conditions: The new plant is xeromorphic and survives well with minimal water once established.

Winter hardiness: The new plant is estimated to be hardy at least from USDA zone 10. Full extent of winter hardiness has not been tested.

It is claimed:

1. A new and distinct cultivar of ornamental x *Mangave* plant named 'Sweet Tooth' as herein described and illustrated.

* * * * *